US005458139A

United States Patent [19]
Pearl

[11] Patent Number: 5,458,139
[45] Date of Patent: Oct. 17, 1995

[54] LOW PROFILE TRACHEOSTOMY TUBE ASSEMBLY

[75] Inventor: Ian A. Pearl, Ft. Lauderdale, Fla.

[73] Assignee: Pearl; Susan O., Ft. Lauderdale, Fla.

[21] Appl. No.: 112,943

[22] Filed: Aug. 30, 1993

[51] Int. Cl.[6] ................................................ A61M 16/00
[52] U.S. Cl. ................... 128/207.14; 128/200.26; 128/911; 128/912; 128/DIG. 26
[58] Field of Search ............... 128/207.14, 207.16, 128/207.17, 207.18, 200.26, 207.15, 911, 912, DIG. 26, 207.29, 205.12, 204.17, 201.13

[56] References Cited

U.S. PATENT DOCUMENTS

| 3,039,469 | 6/1962 | Fountain | 128/207.17 |
|---|---|---|---|
| 3,236,236 | 2/1966 | Hudson | 128/207.17 |
| 3,824,999 | 7/1974 | King | 128/207.17 |
| 4,320,754 | 3/1982 | Watson et al. | 128/204.25 |
| 4,510,933 | 4/1985 | Wendt et al. | 128/207.14 |
| 4,596,248 | 6/1986 | Lieberman | 128/207.16 |
| 4,787,655 | 11/1988 | Gross et al. | 128/207.16 |
| 5,027,811 | 7/1991 | Tuxill | 128/207.17 |
| 5,042,468 | 8/1991 | Lambert | 128/200.24 |
| 5,067,496 | 11/1991 | Eisele | 128/207.14 |
| 5,184,611 | 2/1993 | Turnbull | 128/912 |
| 5,222,491 | 6/1993 | Thomas | 128/204.18 |
| 5,259,376 | 11/1993 | Bales | 128/207.17 |
| 5,282,463 | 2/1994 | Hammersley | 128/207.17 |
| 5,285,775 | 2/1994 | Mayer | 128/205.13 |
| 5,305,742 | 4/1994 | Styers et al. | 128/207.17 |

FOREIGN PATENT DOCUMENTS

| 216569 | 8/1958 | Australia | 128/207.14 |
|---|---|---|---|
| 2007789 | 5/1979 | United Kingdom | 128/207.14 |

Primary Examiner—Edgar S. Burr
Assistant Examiner—William J. Deane, Jr.
Attorney, Agent, or Firm—Robert M. Downey

[57] ABSTRACT

A tracheostomy tube assembly including an outer cannula having a hollow tube-shaped body with an interior passage therethrough, an open distal end, and a proximal end zone including an open proximal end; an inner cannula having a hollow tube-shaped body having an air flow channel therethrough, a first open end and an opposite second end zone including an open second end, the inner cannula being structured for fitted, sliding receipt within the inner passage of the outer cannula such that the second end zone protrudes from the open proximal end of the outer cannula. A circuit connector head includes an airflow passage therethrough extending between an open bottom end adapted for vertical interconnection with the ventilator circuit of a ventilator system and a main face substantially perpendicular to the open bottom with an open port therethrough, the open port being structured for airtight attachment to the proximal end zone of the outer cannula such that the air flow passage is disposed in fluid flow communication with the air flow channel of the inner cannula and the ventilator circuit.

7 Claims, 2 Drawing Sheets

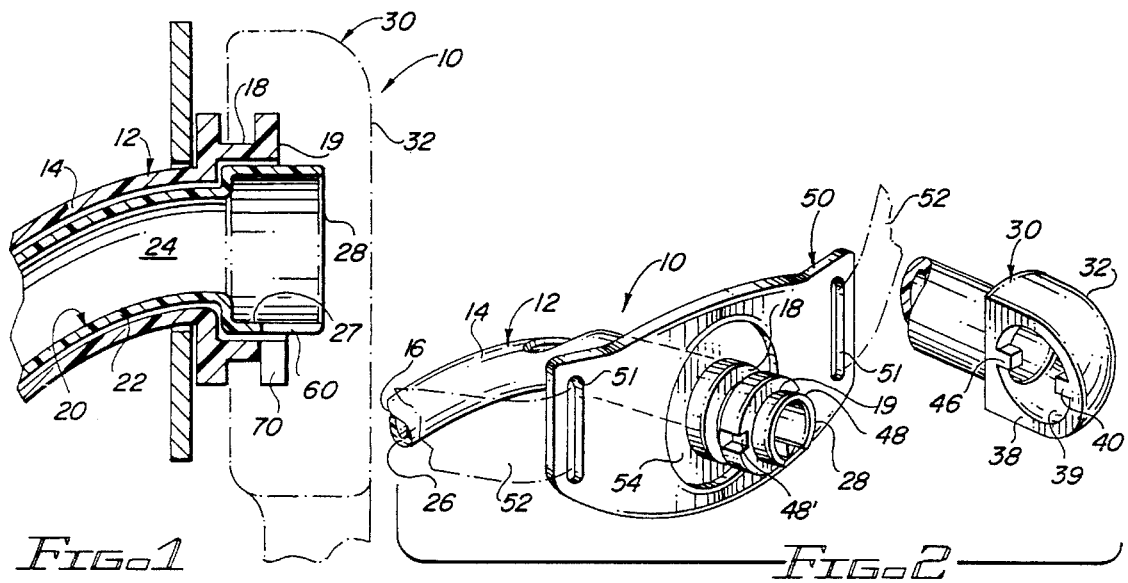
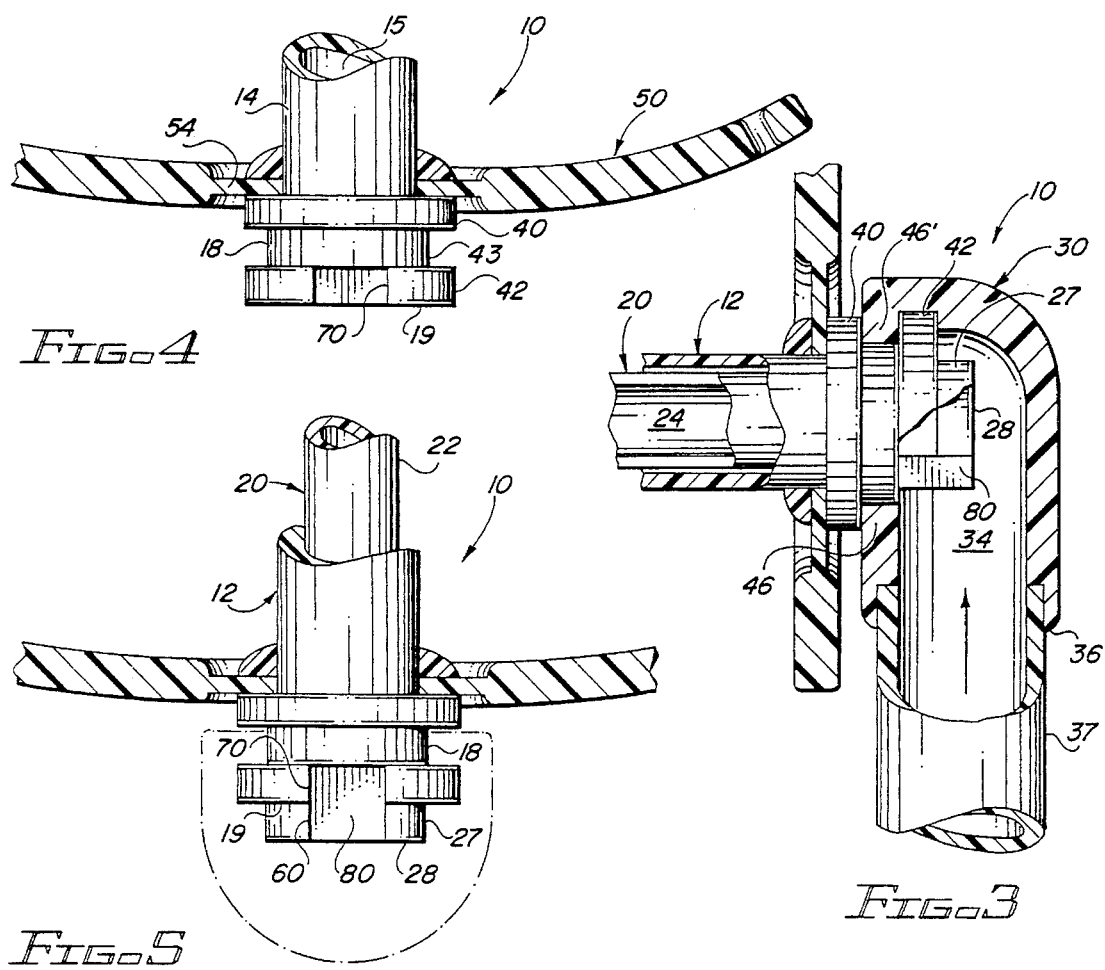

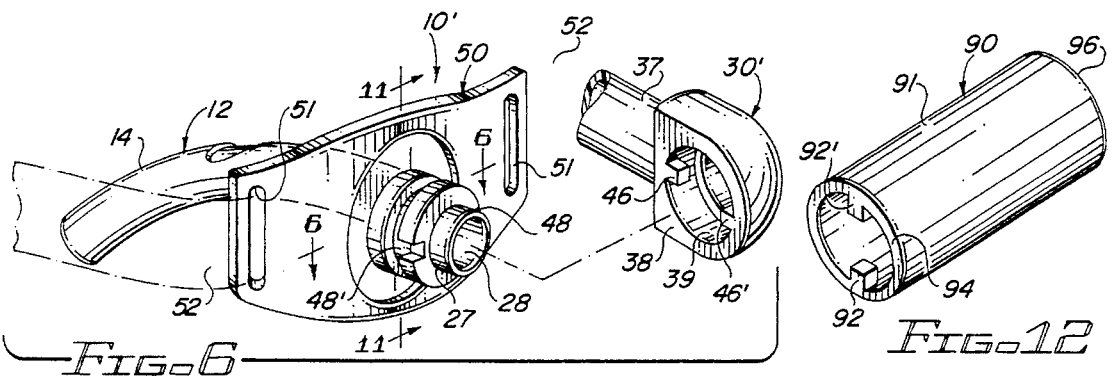
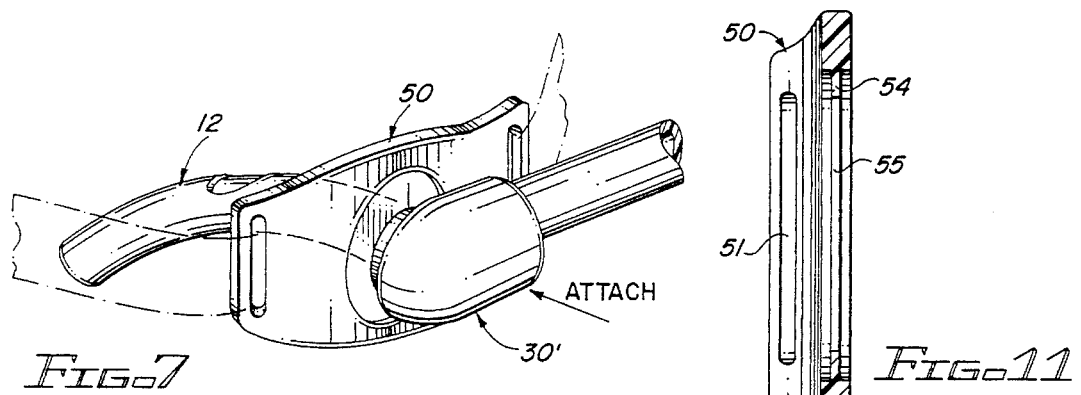
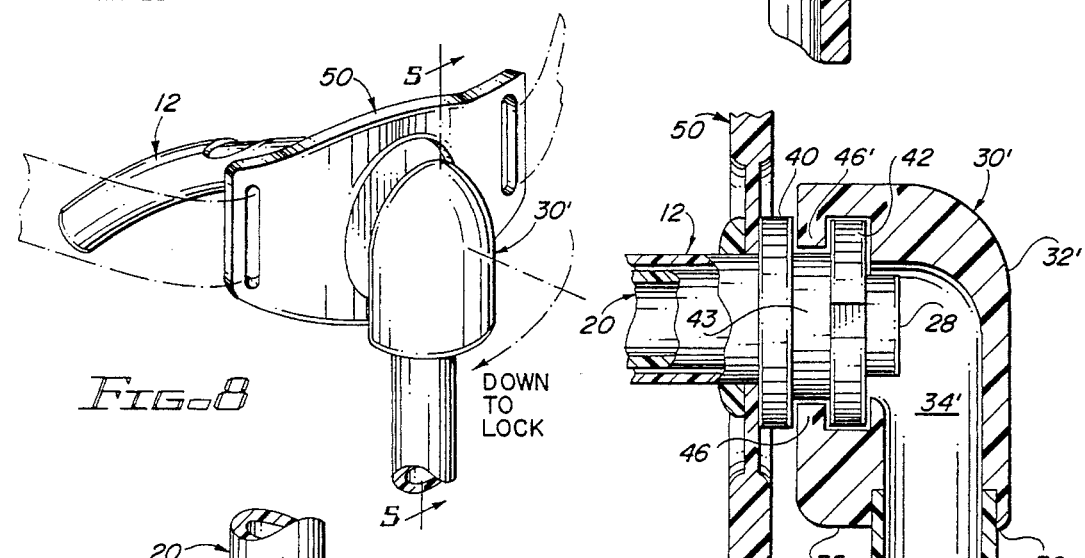
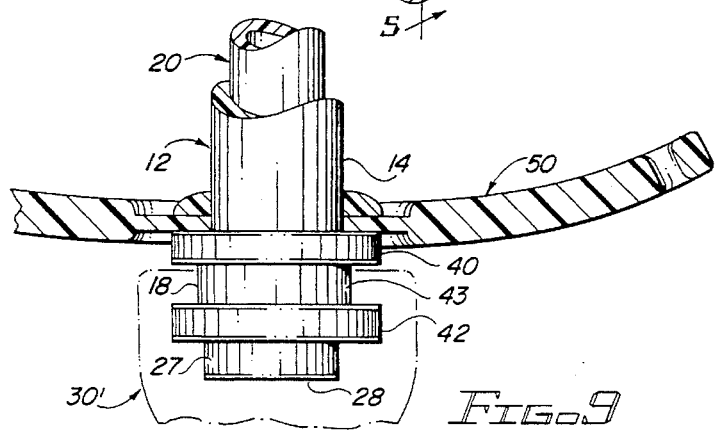

LOW PROFILE TRACHEOSTOMY TUBE ASSEMBLY

BACKGROUND OF THE INVENTION

1. Field of the Invention

The present invention relates to tracheostomy tube assemblies adapted for interconnection with a ventilator circuit in such a manner so as to minimize the amount of protrusion from a user's neck.

2. Description of the Related Art

Individuals who have undergone tracheostomy procedures, due to various respiratory complications and disorders, require the use of a tracheostomy tube assembly in combination with a mechanical ventilator system to assist their breathing. Many times, the need to use a mechanical ventilator is long term, requiring the individual to use a permanent tracheostomy tube assembly along with a portable ventilator. Current existing tracheostomy tube designs, however, are physically cumbersome, uncomfortable, and aesthetically unacceptable, especially to the user. The standard ventilator circuit connectors utilized in connection with the presently used tracheostomy tube assemblies for connection of the tracheostomy tube with the mechanical ventilator require a substantial length of protrusion from the user's neck in order to make a secure, airtight connection. This protrusion is usually several inches, extending outwardly, perpendicular to the user's neck and trachea. This extensive protrusion is highly visible and does not lend itself to covering with a shirt or scarf, thereby resulting in a continuous source of discomfort for individuals who otherwise enjoy participation in public activity. In addition to the psychological discomfort both to the user and persons encountered by the user, the extensive protrusion also provides physical discomfort, making it significantly difficult for the user to easily turn their head without obstruction, and to otherwise maneuver without contacting and potentially dislodging the connection. Accordingly, with the increased mobility available to patients having a permanent tracheostomy, through the use of a portable ventilator assembly and the like, it would be highly beneficial to provide a tracheostomy tube assembly which in addition to being functionally effective, provides a minimal amount of protrusion from a user's neck enabling the assembly to be easily covered or concealed with a shirt collar or scarf. The assembly of the present invention provides such a low profile tracheostomy tube assembly which, while functioning with the equivalent effect and ease of existing tracheostomy tube assemblies, provides an aesthetically pleasing and efficient exterior connection, minimizing the visibility of the assembly.

SUMMARY OF THE INVENTION

The present invention is directed to a low profile tracheostomy tube assembly for use by individuals who have undergone tracheostomy procedures, thereby necessitating the use of artificial breathing aids such as portable mechanical ventilators. The tracheostomy tube assembly of the present invention includes an outer cannula defined by a hollow tubular member adapted for passage through a patient's neck downwardly through the trachea. The outer cannula includes a proximal end zone which normally extends exteriorly from the patient's neck. An open distal end and an opposite open proximal end of the outer cannula are disposed in fluid communication with an interior passage extending therethrough. An inner cannula defined by a hollow tubular member being sized and configured for sliding, fitted receipt within the interior passage of the outer cannula, includes open opposite ends disposed in fluid communication with an airflow channel extending therethrough. The inner cannula includes a first end zone which is structured to protrude from the open proximal end of the outer cannula when the inner cannula is disposed in fitted relation therein.

A circuit connector head includes an open bottom end adapted for fitted attachment of a ventilator circuit hose thereto. A main face on the circuit connector head includes an open port therethrough, the central axis of which is substantially perpendicular to a central axis of the open bottom end. The open port on the main face is specifically structured for fitted, locking attachment to the proximal end zone of the outer cannula such that the protruding first end zone of the inner cannula is disposed in encapsulated relation within an airflow passage in the circuit head connector in fluid communication with the open bottom end. Attachment means are provided to enable secure, locking engagement of the circuit head connector to the proximal end zone of the outer cannula.

In a first embodiment, a bottom half of the first end zone of the inner cannula, protruding from the proximal end of the outer cannula, includes a cutout portion to permit airflow therethrough. A portion of the bottom of the proximal end zone of the outer cannula is also cutout so as to align with the cutout portion on the first end zone of the inner cannula, thereby providing for a sufficient airflow-through means. In this manner, an air supply directed upwardly through the open bottom of the circuit connector head can be effectively and efficiently directed through the inner cannula and subsequently into the trachea, without requiring a substantial horizontal protruding section from the patient's neck in order to affect the directional change of the airflow.

In another preferred embodiment of the present invention, the airflow passage within the circuit connector head is specifically structured and configured to affect a directional change in the airflow therethrough so as to effectively direct the airflow through the inner cannula, while maintaining a minimal amount of protrusion from the patient's neck.

With this in mind, it is a primary object of the present invention to provide a low profile tracheostomy tube assembly which is structured to minimize the amount of protrusion of the tracheostomy tube assembly exteriorly from the patient's neck, and enabling air supply from a ventilator circuit to be directed vertically upward to the protruding end of the tracheostomy tube assembly, rather than horizontally in line with the tube assembly.

It is another object of the present invention to provide a low profile tracheostomy tube assembly which is adapted for use with existing mechanical ventilators and ventilator circuits.

It is a further object of the present invention to provide a low profile tracheostomy tube assembly which is not highly visible and which can be easily concealed by a shirt collar, turtleneck or scarf.

It is still a further object of the present invention to provide a low profile tracheostomy tube assembly which is structured to provide increased comfort to a patient, enabling the patient to function in public areas without cumbersome and unattractive protruding assemblies extending substantially from their neck.

BRIEF DESCRIPTION OF THE DRAWINGS

For a fuller understanding of the nature of the present invention reference should be had to the following detailed description taken in connection with the accompanying drawings in which:

FIG. 1 is a partial sectional view of a first preferred embodiment of the tracheostomy tube assembly of the present invention.

FIG. 2 is a perspective view of the tracheostomy tube assembly of the present invention illustrating attachment of a circuit connector head to an exposed end of the outer cannula.

FIG. 3 is a side plan view, shown in partial section of the tracheostomy tube assembly with the circuit connector head attached to the outer cannula.

FIG. 4 is a top plan view, shown in partial section of the outer cannula fitted to a collar plate of the present invention.

FIG. 5 is a top plan view, in partial section, with the inner cannula fitted within the outer cannula, illustrating an airflow through means formed by mating cutout portions in the inner and outer cannulas.

FIG. 6 is a perspective view illustrating an alternative embodiment of the tracheostomy tube assembly of the present invention.

FIG. 7 and FIG. 8 are perspective views illustrating the manner of attachment, in sequence, of the circuit connector head to the outer cannula, for each of the embodiments of the invention.

FIG. 9 is a top plan view, in partial section, with the inner cannula fitted within the outer cannula and circuit connector head attached thereto.

FIG. 10 is a side plan view, in partial section, of the tracheostomy tube assembly of FIG. 6 with the circuit connector head lockingly attached to the end of the outer cannula.

FIG. 11 is a sectional view of the collar plate taken along line 11—11 of FIG. 6.

FIG. 12 is a perspective view illustrating an AMBU-BAG adapter fitting to facilitate attachment of an AMBU-BAG to the exposed end of the outer cannual in order to perform a tracheal suction procedure.

Like reference numerals refer to like parts throughout the several views of the drawings.

DETAILED DESCRIPTION OF THE PREFERRED EMBODIMENTS

Referring initially to FIGS. 1–5, there is illustrated a first preferred embodiment of the tracheostomy tube assembly of the present invention, generally indicated as 10. The tracheostomy tube assembly 10 includes an outer cannula 12 having a hollow, tube shaped body 14 with interior passage 15 therethrough. The outer cannula 12 is adapted to be surgically fitted through a patient's neck and into the trachea terminating at an open distal end 16 within the trachea. An opposite proximal end zone 18 and open end 19 remains exterior of the patient.

An inner cannula 20, having a hollow, tubular body 22 substantially congruent to the outer cannula body 14, is specifically structured for sliding, fitted receipt within the interior passage 15 of the outer cannula 12. In order to permit receipt of the inner cannula 20 within the outer cannula 12 the inner cannula body 22 has an outermost diameter slightly smaller than the inner diameter of the tube shaped body 14 of the outer cannula 12. An airflow channel 24 extends between opposite open ends of the inner cannula 20 and is specifically structured to facilitate airflow through an open end 28 and out through an opposite open distal end 26 within the trachea. An end zone 27 of the inner cannula 20 is specifically structured and configured to fit within the proximal end zone 18 of the outer cannula so as to partially protrude outwardly therefrom, exposing the open end 28.

A circuit connector head 30 is specifically structured to facilitate a low profile connection of the ventilator circuit of the ventilator system to the proximal end zone 18 of the outer cannula so as to direct airflow through the open end 28 of the inner cannula 20. The circuit connector head 30 is specifically designed to facilitate connection of the ventilator circuit to the tracheostomy tube assembly in such a manner as to minimize the horizontal length of protrusion from the patient's neck. In order to do this, the circuit connector head attaches the ventilator circuit in a vertical direction, rather than horizontally in line with the end of the inner cannula. The circuit connector head 30 includes a main body 32 which is specifically designed to have a shallow depth so as to extend only slightly beyond the end 28 of the inner cannula 20 when attached to the proximal end zone 18 of the outer cannula 14, as best seen in FIG. 1. The main body 32 of the circuit connector head 30 includes an airflow passage 34 extending therethrough between an open bottom end 36 and an opposite open port 39 formed in a main face 38. The plane of the main face 38 is substantially perpendicular to the plane of the open bottom end 36 so as to effectively achieve a 90 degree change in direction through the airflow passage 34. An extension segment 37 may be fitted to the open bottom end 36 to better facilitate attachment of the ventilator circuit thereto. In this manner, the attachment segment 37 would be structured and configured for airtight attachment to an open free end of the ventilator circuit.

Attachment means are provided to facilitate locking attachment of the circuit connector head 30 to the proximal end zone 18 of the outer cannula 12, as best seen in FIG. 3. The attachment means includes a lock ring fitting on the proximal end zone 18 including a first annular ring 40 and a second annular ring 42 about the open end 19 in spaced relation to the first annular ring 40 so as to form a groove 43 therebetween. A pair of lugs 46, 46' are provided within the open port 39 on the connector head, the lugs 46, 46' being structured and disposed for passage through corresponding slots 48, 48' on the second ring 42 such that the protruding end portion 27 and open end 28 of the inner cannula extends within the airflow passage 34 of the connector head 30. Locking attachment of the connector head 30 to the proximal end zone 18 is achieved by positioning the lugs 46, 46' within the groove 43 between the inner and outer ring 40 and 42 and then rotating the connector head 30 approximately 90 degrees, as illustrated in FIGS. 7 and 8. In this manner, an airtight seal is created, wherein the circuit connector head 30 is lockingly fitted to the proximal end zone 18 as shown in FIG. 3.

In the embodiment of FIGS. 1–5, the amount of horizontal protrusion from the patient's neck is further minimized by providing an airflow through means in the bottom half of the ends of the outer and inner cannulas which extend within the airflow passage 34 of the circuit connector head 30. A first cutout portion 60 is formed in the bottom half of the end zone 27 of the inner cannula, as best seen in FIGS. 2 and 5. A corresponding second cutout portion 70 is formed in the bottom half of the second annular lock ring 42 being structured and disposed for mating alignment with the first cutout portion 60 so as to form a window 80 facilitating uninterrupted airflow from the airflow passage 34 through the airflow channel 24 of the inner cannula 20, as seen in FIG. 3. In this manner, the depth of the circuit head connector body 32 is minimized, eliminating the need for the circuit connector head 30 to extend substantially beyond the open end 28 of the inner cannula in order to effect a directional change in airflow from a substantially vertical direction to a substantially horizontal direction into the airflow channel 24 of the inner cannula 20.

A collar plate 50 is further provided to prevent undesirable movement of the tracheostomy tube assembly from its position within the patient's trachea. The collar plate 50 is structured to engage the patient's neck surrounding the outer cannula 12 and includes slots 51 at opposite ends for attachment of a retaining strap 52 which extends about the patient's neck, maintaining the collar plate and tracheostomy tube assembly in place. A central zone 54 includes an aperture 55 therethrough for fitted passage of the outer cannula 12 throught the collar plate 50. The central zone 54 is specifically structured to absorb any force exerted on the tracheostomy tube assembly which would otherwise cause painful movement of the inner and outer cannulas within the trachea.

Referring now to FIGS. 6, 9, and 10, there is illustrated an alternative embodiment of the present invention which is substantially similar to the embodiment shown in FIGS. 1–5 with the exception of the cutout portions 60 and 70 in the end zones of the inner and outer cannulas. Additionally, the circuit connector head 30' is modified to achieve a 90 degree change in directional flow through the airflow passage 34'. As seen in FIG. 10, the body 32' of the circuit connector head 30' is slightly larger than the circuit connector head 30 of the first embodiment and includes a bottom face 35 with bottom opening 36 therethrough. The airflow passage 34' extends upwardly from the bottom opening 36 and then bends sharply to direct airflow through the open end 28 of the inner cannula 20.

In order to facilitate attachment of an AMBU-BAG to either of the embodiments of FIGS. 1–5 and FIGS. 6, 9, and 10, an AMBU-BAG adapter 90 is provided, as shown in FIG. 12. The AMBU-BAG adapter 90 includes a cylindrical body 91 with open opposite ends including a first end 94 and a second end 96. The first end 94 is structured for attachment within the groove 43 between lock rings 40, 42 on the proximal end zone 18 of the outer cannula. The first end 94 includes attachment lugs 92, 92' which are structured and disposed for passage through the slots 48, 48' so as to engage within the groove 43, whereupon subsequent rotation thereof facilitates locking attachment in much the same manner as the attachment of the circuit connector head 30. An AMBU-BAG is attachable to the opposite end 96 so that a trachea suctioning procedure may be performed.

Now that the invention has been described,
What is claimed is:

1. A tracheostomy tube assembly for use with a ventilator system including a ventilator circuit, said assembly comprising:

an outer cannula including a hollow tubular body having an open distal end and a proximal end zone including an open proximal end, an inner cannula including a hollow tubular body structured and configured for sliding, fitted receipt within said outer cannula and including a first end zone having an open first end, an opposite open second end and an airflow channel therebetween, said first end zone being structured and disposed to at least partially protrude from said open proximal end of said outer cannula when said inner cannula is fitted therein, a circuit connector head including an open bottom end adapted for interconnection with the ventilator circuit of the ventilator system, and a main face disposed in substantially perpendicular relation to said open bottom end and including an open port therethrough and having a locking member, said circuit connector head further including an airflow passage between and in fluid communication with said open bottom end and said open port, said first end zone of said inner cannula including a cutout portion on a bottom half thereof, said cutout portion being structured and configured to facilitate fluid airflow between said airflow passage of said circuit connector head and said airflow channel of said inner cannula, said proximal end zone of said outer cannula including a second cutout portion on a bottom half thereof being sized and configured for mating alignment with said cutout portion on said inner cannula so as to further facilitate fluid airflow between said airflow passage of said circuit connector head and said airflow channel of said inner cannula, and attachment means for fitted attachment of said circuit connector head to said proximal end zone of said outer cannula such that said airflow passage is disposed in fluid communication with said airflow channel of said inner cannula, said attachment means including at least one annular lock ring disposed about said proximal end zone of said outer cannula and including at least one notch formed therein for releasable passage of said corresponding locking member on said main face therethrough, said locking member being structured for locking engagement with an inner surface of said annular lock ring to effectively attach said circuit connector head to said proximal end zone of said outer cannula.

2. A tracheostomy tube assembly as set forth in claim 1 further including a collar plate having a central opening therein structured and configured for secured receipt of said outer cannula therethrough, said collar plate being structured and disposed to contact a user's neck such that said proximal end zone of said outer cannula protrudes from and is maintained externally of the user.

3. A tracheostomy tube assembly as set forth in claim 1 wherein said attachment means includes a plurality of notches formed in said annular lock ring and a plurality of corresponding locking members, wherein each of said notches is specifically structured and disposed for releasable passage of a corresponding one of said locking members therethrough to facilitate attachment of said circuit connector head to said proximal end zone of said outer cannula.

4. A tracheostomy tube assembly as set forth in claim 3 wherein said circuit connector head is structured and disposed to encapsulate said first end zone of said inner cannula when attached to said proximal end zone of said outer cannula, such that said first end zone is positioned within said airflow passage permitting fluid communication between said airflow passage and said airflow channel of said inner cannula.

5. A tracheostomy tube assembly as set forth in claim 1 further including AMBU-BAG attachment means for attachment of an AMBU-BAG to said proximal end zone of said outer cannula, said AMBU-BAG attachment means including a cylindrical body having a first end structured for locking, airtight attachment to said proximal end zone and an opposite second end structured for attachment of an AMBU-BAG thereto to facilitate performing a trachea suction procedure.

6. A tracheostomy tube assembly for use with a ventilator system including a ventilator circuit, said assembly comprising:

an outer cannula including a hollow tubular body having an open distal end and a proximal end zone including an open proximal end, an inner cannula including a hollow tubular body structured and configured for sliding, fitted receipt within said outer cannula and including a first end zone having an open first end, an opposite open second end and an airflow channel therebetween, said first end zone being structured and disposed to at least partially protrude from said open proximal end of said outer cannula when said inner cannula is fitted therein, a circuit connector head including an open bottom end adapted for interconnection with the ventilator circuit of the ventilator system, and a main face disposed in substantially perpendicular relation to said open bottom end and including an open port therethrough and having a locking member structured to attach circuit connector head to said proximal end zone of said outer cannula, said circuit connector head further including an airflow passage between and in fluid communication with said airflow channel of said inner cannula, said first end zone of said inner cannula including a cutout portion on a bottom half thereof, said cutout portion being structured and configured to facilitate fluid airflow between said airflow passage of said circuit connector head and said airflow channel of said inner cannula, said proximal end zone of said outer cannula including a second cutout portion on a bottom half thereof being sized and configured for mating alignment with said cutout portion on said inner cannula so as to further facilitate fluid airflow between said airflow passage of said circuit connector head and said airflow channel of said inner cannula, and attachment means for fitted attachment of said circuit connector head to said proximal end zone of said outer cannula such that said airflow passage is disposed in fluid communication with said airflow channel of said inner cannula.

7. A tracheostomy tube assembly as set forth in claim 6 wherein said circuit connector head is structured and disposed to encapsulate said first end zone of said inner cannula when attached to said proximal end zone of said outer cannula, such that said first end zone is positioned within said airflow passage permitting fluid communication between said airflow passage and said airflow channel of said inner cannula.

* * * * *